United States Patent [19]

Kohl

[11] Patent Number: 6,114,857
[45] Date of Patent: Sep. 5, 2000

[54] SYSTEM AND METHOD FOR MONITORING CORROSION IN OILFIELD WELLS AND PIPELINES UTILIZING TIME-DOMAIN-REFLECTOMETRY

[75] Inventor: Kristopher T. Kohl, Houston, Tex.

[73] Assignee: Baker Hughes Incorporated, Houston, Tex.

[21] Appl. No.: 09/264,484

[22] Filed: Mar. 8, 1999

[51] Int. Cl.[7] .......................... G01R 31/11; G01R 31/08; G01V 3/02; G01N 27/26

[52] U.S. Cl. .......................... 324/534; 324/527; 324/368; 204/404

[58] Field of Search .................................. 324/534, 527, 324/543, 544, 700, 368; 422/107; 204/404; 348/84

[56] References Cited

U.S. PATENT DOCUMENTS

| | | | |
|---|---|---|---|
| 4,402,912 | 9/1983 | Krueger | 422/107 |
| 5,680,049 | 10/1997 | Gissler | 324/368 |
| 5,717,337 | 2/1998 | Kelly | 324/534 |

*Primary Examiner*—Safet Metjahic
*Assistant Examiner*—James C Kerveros
*Attorney, Agent, or Firm*—Madan, Mossman & Sriram, P.C.

[57] ABSTRACT

The present invention provides a system and method for in-situ monitoring of corrosion in a conduit which carries fluids that have corrosive effects on the materials utilized for the conduit and/or equipment disposed in the conduit. The conduit may include a well carrying hydrocarbons from subsurface formations or a pipeline transporting hydrocarbons. A cable of sufficient length having a conductor that is susceptible to the corrosive effects of the fluids in the conduit is deployed along a length of the conduit. The conductor is exposed to the fluid continuously or at selected spaced apart locations. The distance of each of the exposed locations from an accessible end is known. A signal generator coupled to the cable induces a pulsed signal into the cable. The transmitted signals are reflected by location on the cable where the impedance differs from the normal impedance. Such locations include each of the exposed conductor locations and the termination point. The reflected signals are received by a receiver and then processed and analyzed by a processor to determine the extent of the corrosion at each of the exposed locations. This information is then used to estimate the nature and extent of the corrosion of components in the wellbore or the pipeline, as the case may be. The cable may be a single conductor cable or a twisted pair of wires, each having a known impedance per unit length.

15 Claims, 3 Drawing Sheets

SYSTEM AND METHOD FOR MONITORING CORROSION IN OILFIELD WELLS AND PIPELINES UTILIZING TIME-DOMAIN-REFLECTOMETRY

BACKGROUND OF THE INVENTION

1. Field of the Invention

This invention relates generally to monitoring and control of corrosion of oilfield wells and oil and gas pipelines, and, more specifically, to the use of time-domain-reflectometry methods for in-situ monitoring of such corrosion.

2. Background of the Art

Wellbores or wells are formed in subsurface formations to recover hydrocarbons trapped in such formations. Such wells are usually lined with a metal (typically steel) liner or casing. Cement is packed in the space (annulus) between the wellbore and the casing. Perforations made in the casing allow the flow of the hydrocarbons from the formations to the casing via the perforations. A tubing disposed inside the casing extending from the surface to a location above the perforations carries the formation fluid containing the hydrocarbons to the surface. A metallic screen is placed between the casing and the tubing to prevent the flow of solids from the formation to the tubing. A number of metallic devices, including fluid flow control valves, safety valves, etc. are disposed in the casing and/or the tubing to facilitate the flow of the formation fluids to the surface. The formation fluid is generally under relatively high pressure (sometimes greater than 10,000 psi) and at relatively high temperature (often above 150° F.). Frequently, formation fluid flows into the wellbore at a relatively high velocity.

The formation fluid often includes corrosive elements, such as salt water and sulfates. Such elements corrode the metallic tubular members and other devices in the wellbores. Corrosion accelerates at high temperatures and pressures. Corrosion inhibits the production of the hydrocarbons and, if not controlled, can destroy the equipment in the well. This can lead to extensive reworking of the well or, in extreme cases, abandoning of the well.

Formation pressure in older wells or at shallow production zones is often not sufficient to cause the formation fluid to rise to the surface. In such wells, electrical submersible pumps are commonly utilized to recover the formation fluid from such wells. Corrosive fluids in the well can be very detrimental to the operation of such relatively expensive equipment.

Oil and gas pipelines carry large amounts of hydrocarbons from the oil and gas fields to the processing plants over great distances. Pump stations along the pipelines move the hydrocarbons through the pipelines. Such hydrocarbons often carry chemicals which corrode the pipelines and the equipment in the pipelines.

A variety of chemicals (also referred to herein as the "additives") are often selectively injected into the fluid flowing through the wells or the pipelines (collectively referred to herein as hydrocarbon-carrying conduits) to inhibit the corrosion. To monitor the corrosion, various devices are periodically inserted into the hydrocarbon-carrying conduits to determine the extent of the corrosion. In one method, a sacrificial corrosion measuring device is conveyed into the wellbore to a selected depth. The device is retrieved after a known time period and analyzed. The corrosion in the wellbore is estimated from the corrosion of the sacrificial device. In another method, samples of the wellbore fluid are taken downhole and analyzed to estimate the corrosive effects on the liner and other devices in the wellbore. In another method, eddy current devices carried by wireline tools are run though the well to determine the pits, cracks and voids in the well liner.

The above-noted and other prior art methods usually require periodic trips to the well site or to the pumping station for the deployment of the corrosion monitoring tools in the wellbore or pipeline to measure corrosion effects. The test results are analyzed to determine the corrective actions, which may include remedial actions, such as workover, replacement or repair of equipment, addition of chemicals into the wellbore or the pipeline, etc. Such corrosion-measuring methods are relatively expensive and do not provide in-situ measurements for quick action.

The present invention provides a system and method for periodic and/or continuous in-situ monitoring of corrosion in wellbores and pipelines. The system can automatically adjust the amounts of chemicals introduced into the wellbores or pipelines based on the in-situ measurements.

SUMMARY OF THE INVENTION

The present invention provides a system and method for in-situ monitoring of corrosion in a conduit which carries fluids that have corrosive effects on the materials utilized for the conduit an/or equipment disposed in the conduit. The conduit may include a well carrying hydrocarbons from subsurface formations or a pipeline transporting hydrocarbons. A cable of sufficient length having a conductor that is susceptible to the corrosive effects of the fluids in the conduit is deployed along a length of the conduit. The conductor is exposed to the fluid continuously along its length or at selected spaced apart locations. The distance of each of the exposed locations from an accessible end is known. A signal generator coupled to the cable induces a pulsed signal into the cable. The transmitted signals are reflected by locations on the cable where the impedance differs from the normal impedance of the cable. Such locations include each of the exposed conductor locations and the termination point. The reflected signals are received by a receiver and then processed and analyzed to determine the extent of the corrosion at each of the exposed conductor locations. This information is then used to estimate the nature and extent of the corrosion of components in the wellbore or the pipeline, as the case may be. The cable may be a single conductor cable or a twisted pair of wires, each having a known impedance per unit length.

In one embodiment, the system of the present invention further includes a chemical injection unit that is adapted to inject selected additives into the conduit to inhibit the corrosive effects of the fluids flowing through the conduit on the wellbore or pipeline equipment in the conduit. The types of the chemicals and their respective injection amounts are determined at least in part based on the extent of the corrosion of the cable measured by the system. The system monitors the amount of the injected chemicals. A common control unit or processor may be utilized to determine the extent of the corrosion in the well and to control the operation of the chemical injection unit.

Examples of the more important features of the invention thus have been summarized rather broadly in order that detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

For detailed understanding of the present invention, reference should be made to the following detailed description of the preferred embodiments, taken in conjunction with the accompanying drawings, in which like elements have been given like numerals, wherein.

DETAILED DESCRIPTION OF PREFERRED EMBODIMENTS

Figure 1:
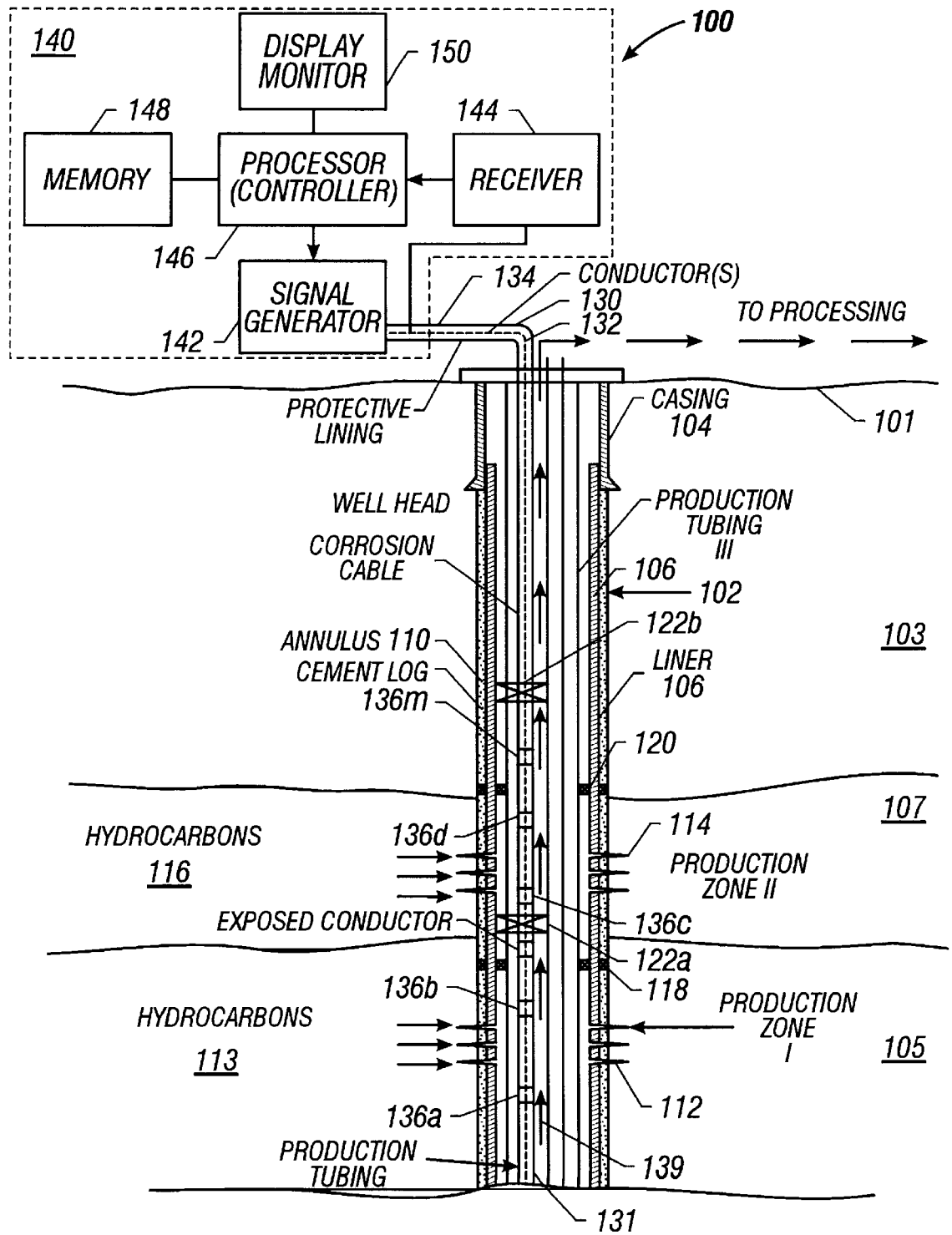
FIG. 1 is a schematic illustration of a corrosion-monitoring system wherein a cable having at least one partially exposed conductor is deployed in a wellbore to make in-situ corrosion measurements using time-domain-reflectometry methods.

FIG. 1 is a schematic illustration of a corrosion monitoring system 100 for making in-situ corrosion measurements of a known conductor deployed in an exemplary production well 102 that carries formation fluids to the surface. The well 102 is drilled from the surface 101. The well 102 penetrates through two exemplary production zones or reservoirs in the earth's subsurface: a lower or deeper reservoir 105 (marked as production zone I in FIG. 1); and an upper or a more shallow reservoir 107 (marked as production zone II in FIG. 1). A relatively large diameter casing 104 is placed in the wellbore from the surface to a relatively shallow depth to avoid collapsing of the well 102 due to relatively soft rock matrix generally found near the surface 101. A metallic liner 106 is placed in the well 102 to a depth that is sufficient to allow the recovery of the hydrocarbons from all of the production the zones. The liner 106 is set in the well 102 by pumping cement 109 into the annulus 110 between the well 102 and the liner 106. A production tubing 111 disposed in the liner 106 carries the formation fluids to the surface 101.

Perforations 112 made in the liner 106 and the adjacent formation 105 allow the formation fluid 113 to flow into the well 102. Similarly, perforations 114 in the liner 106 and the production zone 107 allow the formation fluid 116 to flow from the production zone 107 into the well 102. A packer 118 disposed in the annulus between the liner 106 and the production tubing 111 prevents fluid flow from the lower production zone 105 to the upper production zone 107, and a similar packer 120 prevents fluid communication from the production zone 107 and the surface. The packers 118 and 120 cause all of the produced formation fluids to flow to the surface through the production tubing 111. One or more valves, such as valves 122a and 122b, are suitably disposed in the well to control the flow of the fluids from the various production zones to the surface. Various other equipment (not shown), including safety valves, etc., are also disposed in the production well 102. Such equipment and methods of installing same in wellbores are known in the art and are thus not described in greater detail. The present invention is suitable for any well wherein a fluid in the well has any corrosive effect on any of the equipment in the well.

To determine the corrosive effects of the fluid flowing through the well 102, a cable 130 is deployed in the well 102. In one embodiment of the present invention, the cable 130 has a conductor 136 and an outer protective member or layer 134, which hermetically seals the conductor 136. The cable 130 is designed to have a known impedance per unit length of the cable 130. Any suitable method may be utilized to insert or deploy the cable 130 into the well 102. Several methods are known in the oil and gas industry to deploy cables, tubings and wireline tools in completed wells. The cable 130 terminates at a known end 131. The conductor 136 in the cable 130 is exposed to its surrounding environment continuously or at selected spaced apart locations 136a–136m. At least one of the exposed conductor sections is preferably located adjacent to each of the production zones 105 and 107. Instead of using a single conductor cable 130 as shown in FIG. 1, a twisted pair of shielded wires or any suitable multi-conductor cable may be used, with one wire having certain spaced apart exposed sections. In the exemplary wellbore 102, formation fluid 113 from the lower production zone 105 comes in contact with the exposed sections 136a–136b while the mixture of the fluids 113 and 116 comes in contact with the exposed conductor sections 136c–136m adjacent to the production zone 107. The method of determining the extent of the corrosion of the exposed sections 136a–136m is described below. Once a section of the conductor 136 is excessively corroded, the cable is retrieved. The corrosion of the relatively small exposed sections of the conductor 136 does not significantly reduce the mechanical strength of the cable 130, which allows the cable to be relieved safely. A replacement cable or a cable with different characteristics (electrical, mechanical, and/or chemical) can be deployed in the well 102 by a suitable method as described above.

The fluids from the production zones 105 and 107 may include salt water, sulfates and other matters that can corrode the various materials used for the equipment in the well 102. Different production zones may contain different corrosive elements or different concentration of such elements. It is therefore useful to determine the corrosive effects from each production zone. Further, it is extremely useful to determine the corrosion in-situ at least periodically. In the present invention, the corrosion of the exposed conductor sections 136a–136m is determined in-situ by utilizing a time-domain-reflectometry (TDR) system at the surface, which is described in more detail below. However, it is considered helpful to first describe the basic theory of operation of the TDR systems or methods.

In a TDR system, a pulse of known electrical energy (amplitude and frequency) is transmitted into a cable. When the induced electrical energy reaches the end of the cable or if prior thereto it encounters a change in the electrical properties of the cable "fault", such as change in the impedance, capacitance or inductance, part or all of the induced pulse is reflected back form the end and the fault locations. Prior to any corrosion of the conductor, the system is calibrated so that any reflections occuring due to changes in the capacitance of the cable at the positions of the cuts are identified. Any subsequent-changes in the amplitude and phase of the reflected signals are related to the changes in the resistance of the conductor due to corrosion. The changes in the electrical properties occur due to faults in the cable, including corrosion of the cable. The reflected signals are measured and analyzed to determine the location and the extent of the fault. Signals reflected from the cable end can be easily isolated as the distance of the cable end from the transmission point and the speed of the induced pulse are known. The extent and distance of the faults are determined by analyzing the signatures or spectra of the remaining reflected signals. The distance is easily determined from the time difference between the transmitted signals and the detection of the reflected signals. The extent of the corrosion or corrosion mechanisms can be inferred by analyzing the signatures of the reflected signals. The TDR system can be configured to transmit pulses which will produce reflected signals from such fault locations.

Referring back to FIG. 1, the TDR system 140 of the present invention includes a signal generator 142 that generates pulses of known (predetermined) signature, which are transmitted into the cable 130. The transmitted energy is reflected back to the surface from the exposed wire locations 136a–136m in the well 102. A receiver 144 detects or receives the reflected signals. The signatures of the reflected signals are analyzed by a processor 146. The system further includes one or more memory units 148 for storing data and programs for the processor 146. A display unit or monitor 150 is provided to display the corrosion results for the system 140. The TDR system may be an integrated unit containing the functions described above. Any commercially available or custom designed TDR system may be utilized in this invention.

The TDR system 140 includes programmed instructions and models for analyzing and interpreting the TDR signals. These programs are stored in the memory 148. During the production phase of the well 102, the TDR system 140, at least periodically, transmits the pulses into the cable 130. The reflected signals are detected and analyzed to determine the location and the extent of the corrosion on the cable 130. The system 140 can generate the signals (amplitude and frequency) that are most effective for the given type of the cable and the condition of the cable to obtain reflected signals from each of the exposed sections of the cable 130. Comparison of the signature of the reflected signal from a particular location with reflected signals taken at prior times yields estimates of the extent of the corrosion at such locations. The signals reflected from farther locations, even if they have the same change in the impedance, attenuate more compared to the signals reflected from the closer locations. Calibration data obtained from the unused cable and prior measurements taken in the well is utilized to account for such attenuations in determining the corrosion of the various exposed conductor sections of the cable 130.

The information provided by the system 140 is utilized to estimate corrosive effects in the well 102 and to determine the remedial actions to be taken, including the control of the chemical injection, reworking of the well, removal or replacement of the affected equipment, and retrieval of the cable 130. The periodic in-situ measurements provide early warning about the extent of the corrosion and allow timely remedial actions, which can result in significant cost savings.

Figure 2:
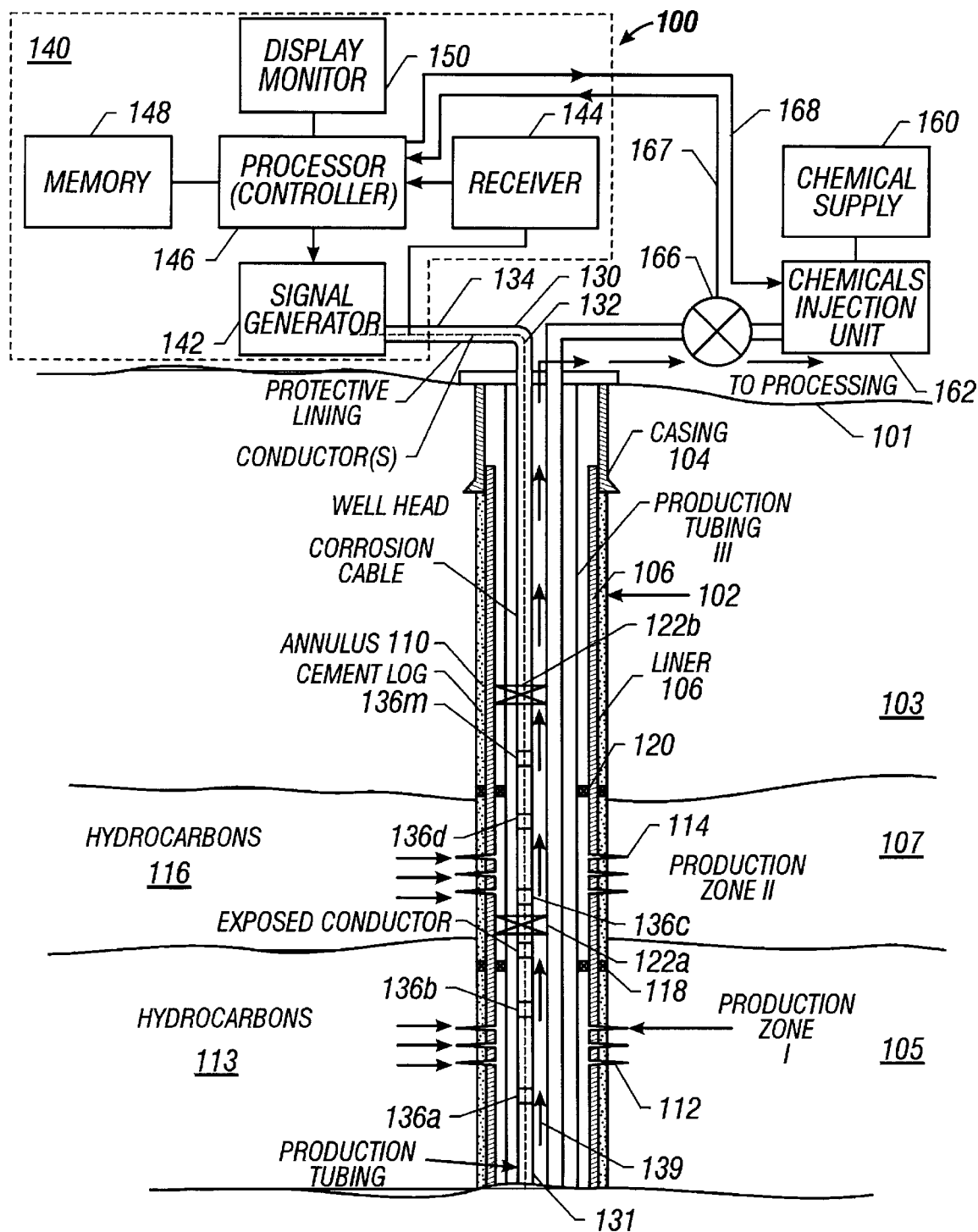
FIG. 2 is a schematic illustration of the corrosion-monitoring system of FIG. 1 with a chemical injection unit system that can automatically adjust the injection of selected chemicals into the wellbore in response to or based on the in-situ corrosion measurements made by the corrosion-monitoring system.

In oilfield wells, chemicals (also referred to in the industry as the "additives" are frequently injected into the wells to inhibit the corrosive effects of the formation fluids on the wellbore equipment. The in-situ corrosion measurement made according to the present invention can be used to control the injection of chemicals to minimize the corrosive effects downhole. FIG. 2 shows a chemical injection system along with the TDR system 140 of FIG. 1. The chemical injection system includes a source of chemicals that supplies one or more of the desired chemicals. A chemical injection control unit 162 controls the injection of the individual chemicals into the wellbore 102 via a conduit 164, which conduit injects the chemicals 160 to one or more selected depths. The amount of the chemicals 160 supplied to the well 102 is measured by a flow device 166, which measurements are provided to the controller 146 via line 167. The controller 146, based at least part on the determination of the corrosion, causes the chemical control unit 162 to adjust the amount and/or the timing of the injection of the chemicals 160. The chemical control unit 162 may be designed to independently control the chemical injection, wherein it communicates with the controller 146 to obtain the corrosion information. The control unit 146 and/or the unit 162 may communicate with a remote unit (not shown), which can provide instructions to the wellsite controllers, which in turn control the chemical injection and provide information about the corrosion in the wellbore.

Figure 3:
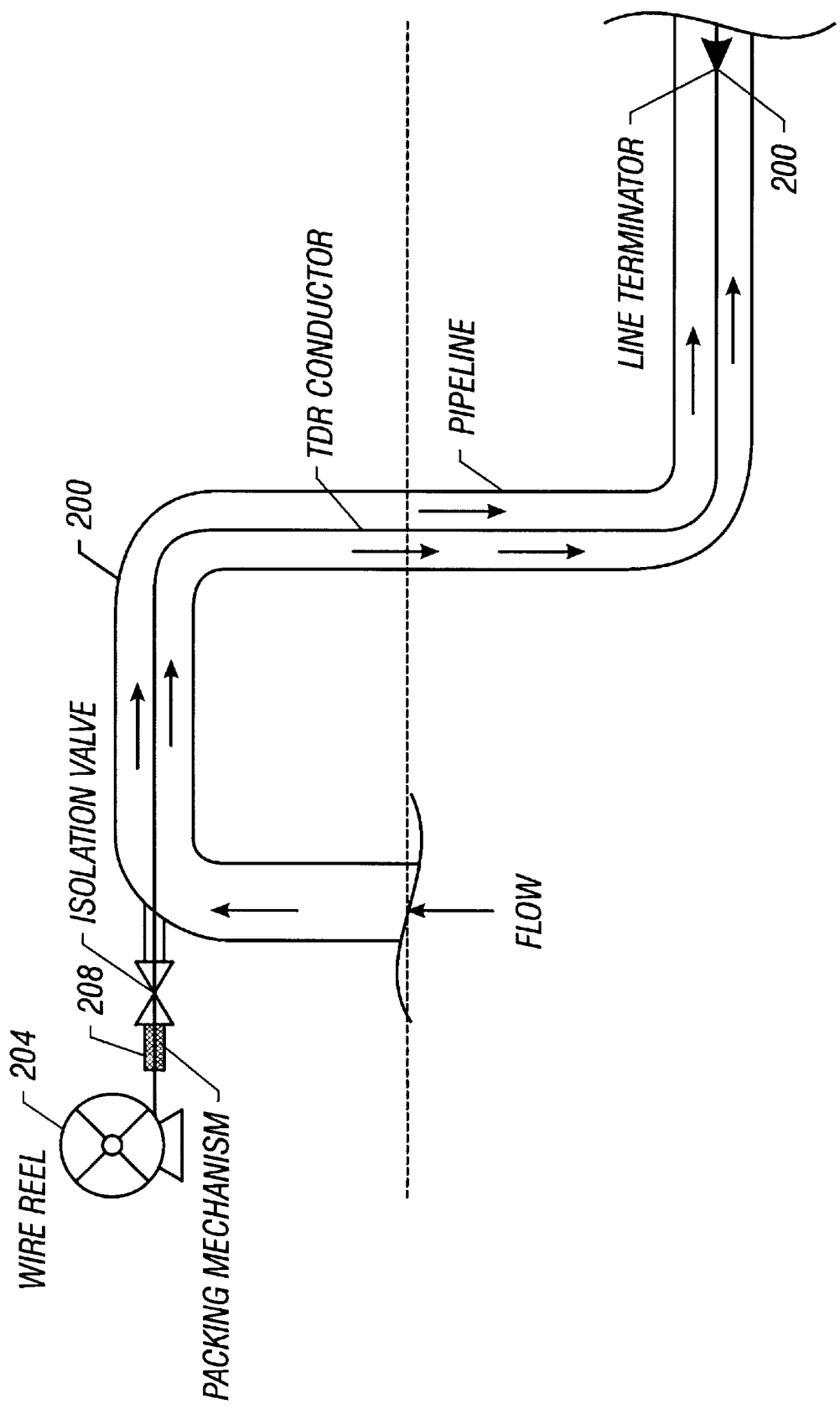
FIG. 3 is a schematic illustration of a pipeline with a cable deployed therein for making corrosion measurements utilizing a time-domain-reflectometry method in the manner shown in FIG. 1.

FIG. 3 shows a section of a pipeline 200 with a cable 202 deployed therein. The TDR cable 202 may be deployed from a reel 204. The cable 202 has a line terminator 205 defining the last reflection point. An isolator valve 206 and a packing mechanism 208 allow safe deployment of the cable 202 into the pipeline 200 and safe retrieval of the cable 202 from the pipeline 200. The TDR system 140 of FIG. 1 may be used for determining the corrosive effects on the cable 202 in the same manner as described in reference to FIG. 1. The desired remedial or corrective actions are taken based on corrosive effects on the pipeline.

In the above described systems, the cable conductor may be made from materials that closely simulate the corrosive effects on the liner material or the pipeline, as the case may be. The system 140 provides early warning of the corrosion along the length of the wellbore or the pipeline. It requires one time deployment of the cable. The TDR cable is left in the conduit for extended time periods. The system does not require periodic insertion and retrieval of any inspection equipment, yet it provides periodic information about the extent of the corrosion along a length of the cable.

While foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A system for monitoring corrosion in a conduit carrying a fluid having a corrosive effect on materials utilized for the conduit or equipment placed in said conduit when said fluid comes in contact with such materials, said system comprising:

(a) a cable of sufficient length deployed in said conduit, said cable having a conductor that is susceptible to the corrosion when said conductor comes in contact with said fluid, said cable having at least one section exposed to said fluid at a predetermined distance from a first end of said cable;

(b) a signal generator coupled to said first end of said cable inducing signals into said cable;

(c) a receiver receiving signals reflected from the at least one exposed section of the conductor; and (d) a processor processing said received signals and providing an indication of the extent of the corrosion of the at least one exposed section of the conductor.

2. The system of claim 1, wherein the at least one exposed section of the conductor is one of (i) a plurality of spaced apart exposed sections, and (ii) a continuously exposed conductor.

3. The system of claim 1, wherein the conduit is one of (i) an oilfield wellbore, and (ii) a pipeline.

4. The system of claim 2, wherein the processor processes the reflected signals from the plurality of the exposed sections and determines the distance corresponding to each such reflection and the extent of the corrosion at the reflection locations.

5. The system of claim 1, wherein the signal generator, receiver and the processor are part of an integral unit.

6. The system of claim 1, wherein the cable is one of (i) a single conductor cable with a known impedance, and (ii) a twisted pair of shielded wires, with one wire having the at least one exposed section.

7. The system of claim 1 further comprising a chemical injection unit that is adapted to inject into the conduit an additive that inhibits the corrosive effect of the fluid on the at least one exposed section of the conductor.

8. The system of claim 7 further comprising a control unit controlling supply of the chemicals to the conduit.

9. The system of claim 8 further comprising a device for measuring the amount of the chemical supplied to the conduit.

10. The system of claim 9, wherein the processor controls the supply of chemicals to the conduit based at least in part on the extent of the corrosive effect on the exposed conductor.

11. A method of monitoring corrosion in a conduit carrying a fluid having corrosive effect on materials utilized to make the conduit or the equipment placed in said conduit, comprising:

deploying a cable of sufficient length in said conduit, said cable having a conductor exposed to the fluid and susceptible to corrosion thereby at at least one location;

inducing a pulsed signal at a first end of said conductor;

detecting a reflected signal from change in impedance of the conductor at the at least one location due to corrosion; and processing said detected signals to determine a measure of corrosion of the at least one exposed section of the conductor.

12. The method of claim 11 further comprising determining a distance of at least one exposed section of the conductor having a change in impedance from the first end of the conductor.

13. The method of claim 11, wherein said conduit carrying a fluid is one of (i) a wellbore carrying fluid from a formation and (ii) a pipeline carrying hydrocarbons therein.

14. The method of claim 11, wherein deploying said cable includes deploying one of (i) a single conductor cable, (ii) a twisted pair of shielded wires with one wire having said at least one exposed section.

15. The method of claim 11, further comprising injecting a chemical into said conduit in response to said determined measurement of corrosion of the at least one exposed section to reduce the corrosive effects of said fluid on said conductor.

* * * * *